United States Patent [19]

Ostojic et al.

[11] 4,008,621
[45] Feb. 22, 1977

[54] METHOD AND APPARATUS FOR SAMPLING GAS

[75] Inventors: Nedeljko Ostojic, Coon Rapids; Vladimir G. Boscak, Minneapolis, both of Minn.

[73] Assignee: Geo. A. Hormel & Co., Austin, Minn.

[22] Filed: July 7, 1975

[21] Appl. No.: 593,871

[52] U.S. Cl. ..................... 73/421.5 R; 23/232 R; 23/259; 73/425.6; 141/25; 222/386.5
[51] Int. Cl.² ........................................ G01N 1/24
[58] Field of Search ............... 23/259, 292, 232 R, 23/254 R; 73/421.5 R, 425.6; 141/25; 222/386.5

[56] References Cited

UNITED STATES PATENTS

| 2,063,430 | 12/1936 | Graser | 222/386.5 X |
| 2,659,516 | 11/1953 | Smith | 222/386.5 X |
| 3,343,422 | 9/1967 | McSmith | 73/425.6 |
| 3,782,198 | 1/1974 | Wachter et al. | 73/421.5 R |
| 3,866,474 | 2/1975 | Hasselmann | 73/421.5 R |

*Primary Examiner*—Norman Yudkoff
*Assistant Examiner*—Barry I. Hollander
*Attorney, Agent, or Firm*—Williamson, Bains & Moore

[57] ABSTRACT

In carrying out the method of sampling gas with our novel apparatus, a user will blow air into an elastic fluid impervious diaphragm which extends into the mouth of a rigid container. As the elastic diaphragm expands inwardly it forces air or gas outwardly of the container through a valve-controlled port, the diaphragm will eventually engage and adhere to substantially the entire inner surface of the container and the valve-controlled port will then be closed. The container will then be placed in a sampling zone and the valve-controlled port will again be opened to communicate with the sampling zone to thereby permit gas to enter and fill the container. The valve-controlled port will then be closed.

1 Claim, 3 Drawing Figures

U.S. Patent  Feb. 22, 1977  4,008,621
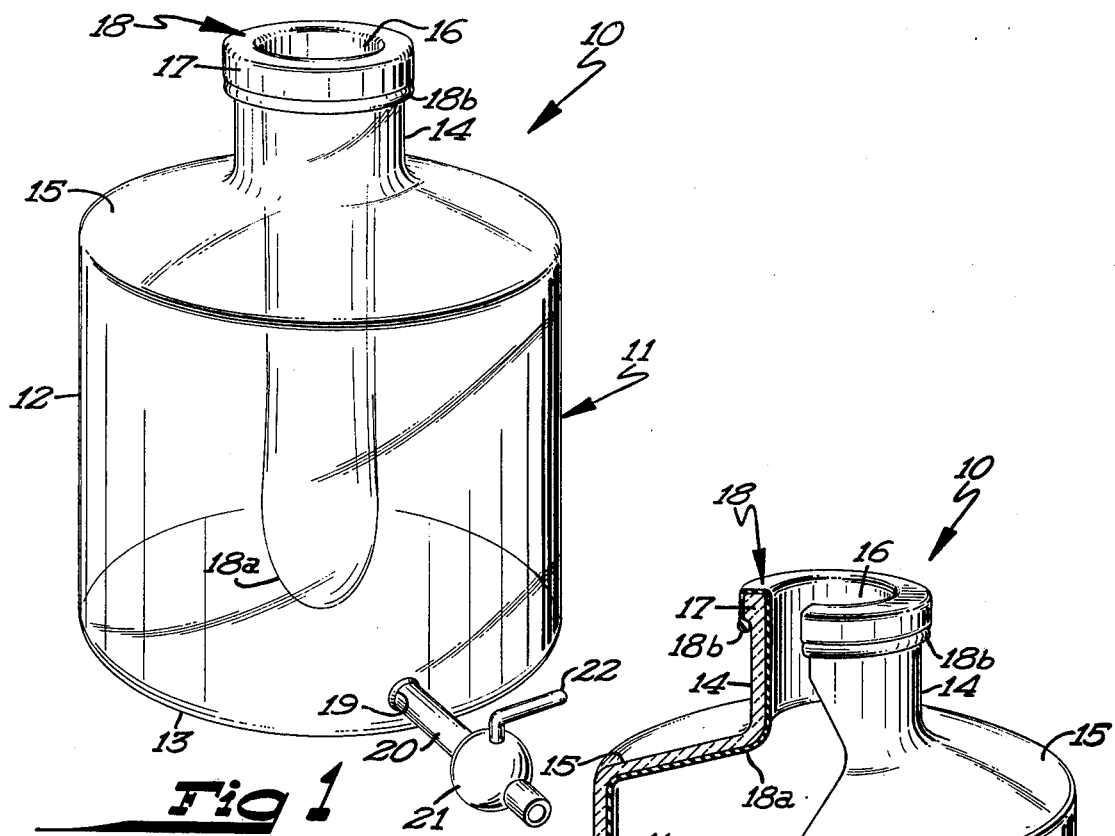
Fig 1
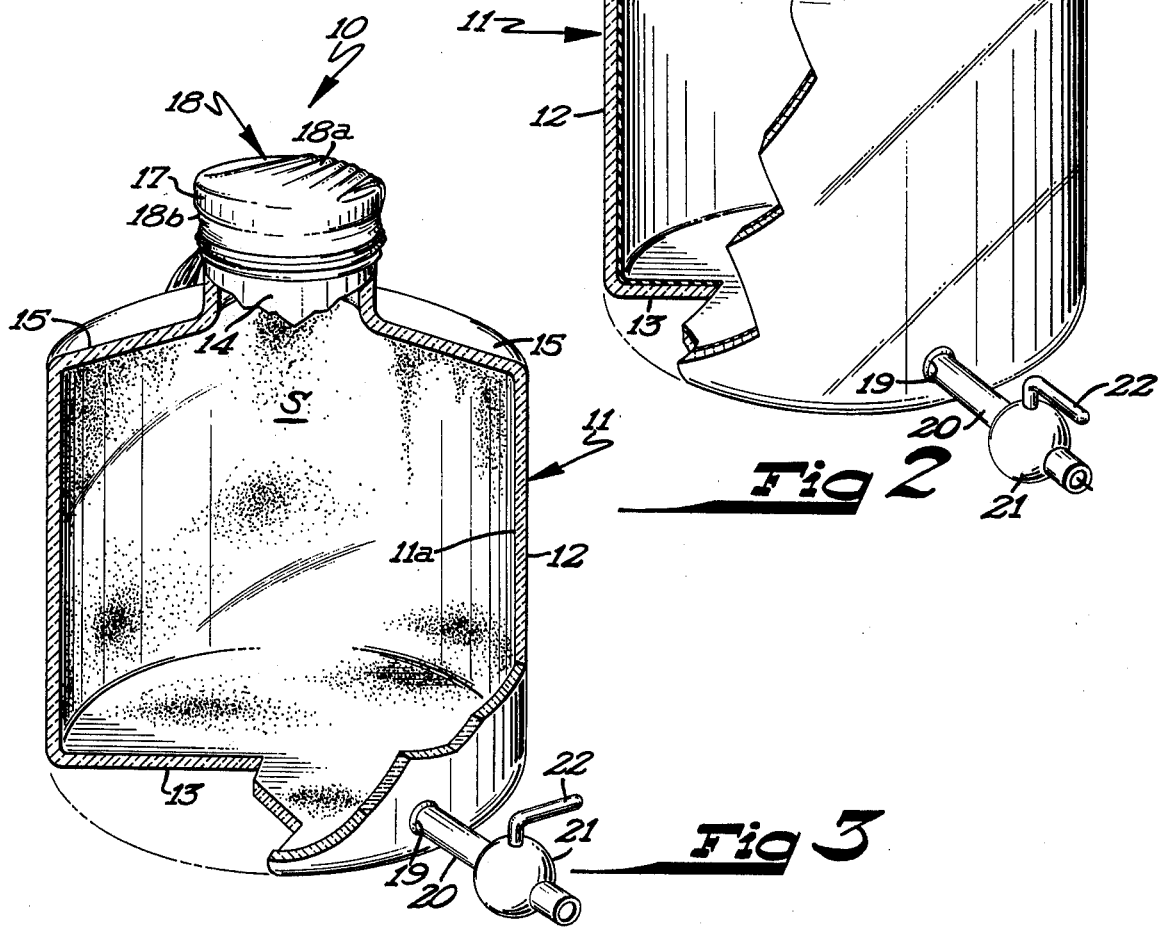
Fig 2
Fig 3

METHOD AND APPARATUS FOR SAMPLING GAS

SUMMARY OF THE INVENTION

This invention relates to the method and apparatus for sampling gas.

It is therefore an object of this invention to provide a novel and improved method and apparatus for sampling gas. Therefore, in accordance with the general object of this invention, we have provided a novel method and apparatus for sampling gas wherein a user simply blows into a fluid-impervious elastic diaphragm which extends into the mouth of a rigid container. The rigid container is provided with a valve-controlled port which is opened to allow air or gas to be evacuated from the container as the elastic diaphragm expands into the container. The fluid-impervious elastic diaphragm will adhere to substantially the entire inner surface of the container when the diaphragm fills the interior thereof. The valve for the port is then closed and the container is taken to a sampling zone where the valve is then again opened. As the diaphragm contracts to its original position, suction or negative pressure is created to cause the gas to enter and fill the container. Then the valve for the port is closed and the sample is obtained.

These and other objects and advantages of this invention will more fully appear from the foregoing description made in connection with the accompanying drawings, wherein like reference characters refer to the same or similar parts throughout the several views.

FIGURES OF THE DRAWINGS

FIG. 1 is a perspective view of the novel sampling device and illustrating the same before air has been evacuated from the interior thereof;

FIG. 2 is a perspective view, similar to FIG. 1 with parts thereof broken away for clarity, but illustrating the condition of the elastic diaphragm after all the air has been evacuated from the interior of the rigid container; and FIG. 3 is a perspective view similar to FIG. 1 with parts thereof broken away and illustrating the sampling device containing the gas sample.

DESCRIPTION OF THE PREFERRED EMBODIMENTS OF THE INVENTION

Referring now to the drawings, it will be seen that one embodiment of the novel sampling device, designated generally by the reference numeral 10 is there shown. The sampling device 10 includes a rigid container 11 which may be constructed of any suitable rigid fluid-impervious material such as glass, metal, plastic or the like. In the embodiments shown, the container 11 includes a substantially cylindrical wall 12, a bottom wall 13, a reduced neck portion 14 which defines a shoulder 15. The upper end of the container 11 is provided with an upwardly opening mouth 16 having a bead of lip 17 at its periphery.

The mouth or opening 16 of the container is closed by a sac-like fluid-impervious elastic diaphragm 18, including a central portion 18a which extends into the opening and which also extends downwardly beyond the lower surface of the lip 17. The elastic diaphragm 18 is provided with an annular retaining element 18b which grips the exterior surface of the neck portion 14 and engages the lower surface of the lip 17. The elastic diaphragm 18 may be formed of any suitable fluid-impervious elastic material such as rubber or the like.

The container 11 is provided with a port or opening 19 in the cylindrical wall 12 thereof adjacent the bottom wall 13 thereof. The port 19 is connected to a conduit 20 having a valve 21 disposed in flow-controlling relation therewith. The valve 21 is provided with an actuator handle 22 which may be manually operated to selectively open and close the valve and to thereby intercommunicate the interior 11a of the container with the exterior. The valve 21 may also be provided with a fitting or coupling element (not shown) which can be connected to an evacuation pump (not shown) if desired. The sampling device 10 may be constructed of any desired size, but it is preferred that it be capable of being easily carried by a user from one location to another.

In carrying out our novel method with the sampling device 10, the interior of the container will be cleaned and dried and will be subjected to atmospheric conditions so that the elastic diaphragm serves to close the mouth or opening 16. The handle 22 of the valve 21 will be moved to the open condition to intercommunicate the exterior with the interior 11a of the container. A user will then blow into the mouth of the container and into the diaphragm to progressively expand the diaphragm into the interior of the container. It will be appreciated that as the diaphragm expands the air or gas within the rigid container will be forced outwardly through valve 21. When the elastic diaphragm fills the interior of the rigid container to engage the entire inner surface of the rigid container, as shown in FIG. 2 of the drawings, the valve 21 will then be closed. After the valve 21 is closed, the diaphragm will remain in engaging relation with the wall of the container until the valve is again opened.

Thereafter, the sampling device will be taken to a sampling zone and the actuator handle 22 will then be shifted to open the valve 21 and to intercommunicate the interior 11a of the container with the sampling zone. When this occurs, the gas in the gas sampling zone will enter the conduit 20 and pass through the port 19 into the interior 11a of the container to fill the container. As gas enters the rigid container through the port, the elastic diaphragm 18 will return to its originally non-expanded condition to thereby create suction or negative pressure to accelerate the filling of the container by the gaseous sample. When the gaseous sample completely fills the container 11, the actuator handle 22 of the valve may then be closed so that the sample will be trapped or collected within the container. The elastic diaphragm may then be stretched tautly across the mouth of the container and then tied in this stretched condition.

It will be appreciated that through the use of the novel sampling device 10, a gaseous sample may be very easily and effectively collected. The evacuation step involves only a minimum time to complete as does the sample collecting step. In some instances, it may be desirable to connect an elongate conduit to the valve 21 so that the open end of the conduit may be inserted into the sampling zone during the sample collecting step. This allows the user to remain at a relative remote position with respect to the sampling zone.

Only two hands are required for the operation, one to hold the sampler and the other to direct the conduit to the right location. Flushing the conduit can be conveniently achieved by forcing the contents of the filled-up container back out. An operator can achieve this by blowing into the mouth of the diaphragm to thereby expand the elastic diaphragm into the container in the manner as described earlier.

From the foregoing description, it will be seen that I have provided a relatively simple and unique method for sampling gas. It will further be seen that my novel sampling device used in carrying out the sample collecting technique is not only of simple and inexpensive construction, but one which functions in a more efficient manner than any heretofore known comparable device.

What is claimed is:

1. A method of obtaining a sample of gas, said method comprising the steps of:

opening a valve controlled port of a rigid portable container with an externally located valve, said rigid container having an upwardly opening reduced diameter neck portion having an opening therein, said neck portion comprising an outer peripheral annular lip portion, a fluid impervious elastic diaphragm extending into and closing said opening, said diaphragm having an annular retaining element for grippingly engaging said container neck lip portion;

directing air into said opening by blowing into said neck to thereby cause the elastic diaphragm to expand into the container to progressively force air from the container out through the port until the diaphragm engages substantially the entire inner surface of the container;

manually closing the valve for said port while said elastic diaphragm engages the inner surface of the container, whereby said diaphragm will adhere to the inner surface of the container;

manually placing the container in the gaseous sampling zone and thereafter manually opening the valve to intercommunicate the container with the sampling zone, whereby the gaseous atmosphere constituting the sampling zone will enter the port and the elastic diaphragm will contract and return to its original position to create suction within the container and cause the gaseous sample to fill the container; and manually closing said externally located valve thereby closing the valve controlled port.

* * * * *